(12) United States Patent
Martuza et al.

(10) Patent No.: US 8,313,896 B2
(45) Date of Patent: Nov. 20, 2012

(54) ONCOLYTIC HERPES SIMPLEX VIRUS IMMUNOTHERAPY IN THE TREATMENT OF BRAIN CANCER

(75) Inventors: Robert L. Martuza, Marblehead, MA (US); Samuel Rabkin, Swampscott, MA (US); William Curry, Boston, MA (US); Christopher Farrell, Brookline, MA (US); Cecile Zaupa, Bassoues (FR)

(73) Assignee: The General Hospital Corporation, Boston, MA (US)

( * ) Notice: Subject to any disclaimer, the term of this patent is extended or adjusted under 35 U.S.C. 154(b) by 61 days.

(21) Appl. No.: 12/384,633

(22) Filed: Apr. 6, 2009

(65) Prior Publication Data

US 2009/0285860 A1 Nov. 19, 2009

Related U.S. Application Data

(60) Provisional application No. 61/123,102, filed on Apr. 4, 2008.

(51) Int. Cl.
*C12Q 1/70* (2006.01)

(52) U.S. Cl. .......................................................... 435/5

(58) Field of Classification Search ........................ None
See application file for complete search history.

(56) References Cited

U.S. PATENT DOCUMENTS 6,429,199 B1* 8/2002 Krieg et al. .................. 514/44 R
2003/0113348 A1* 6/2003 Coffin ........................ 424/230.1

OTHER PUBLICATIONS

Bernhard, et al., Cancer Res 55: 1099 (1995).
Burgdorf et al., Oncol Rep. 20(6): 1305-11 (2008).
Caux et al., Nature 360: 258-261 (1992).
Chang et al., Clin Cancer Res 8: 1021 (2002).
Conti, Immunobiology 213: 859-70 (2008).
Coukos et al., Gene Ther. Mol. Biol. 3: 79-89 (1998).
Geiger et al., Cancer Res 61: 8513 (2001).
Geiger et al., Lancet 356: 1163-1165 (2000).
Hsu et al., Nat. Med. 2: 52-58 (1996).
Inaba et al., Proc. Natl. Acad. Sci USA 90: 3038-42 (1993).
Lim et al., Int. J. Cancer 83: 215-222 (1999).
Lopez et al., J Clin Oncol. 27(6): 945-52 (2009).
Mackall et al., Clin Cancer Res. 14(15):4850-8 (2008).
Miyatake et al., J. Virol. 71: 5124-5132 (1997).
Naik et al., Nature Immunol 8: 1217-26 (2007).
Nestle et al., Nat. Med. 4: 328-332 (1998).
Palmer et al., Hepatology 49(1): 124-32 (2009).
Palucka et al., Immunol Rev. 220: 129-50 (2007).
Palucka et al., J Immunother. 31(9): 793-805 (2008).
Romani et al., J. Exp. Med. 180: 83-93 (1994).
Schuetz et al., Cancer Immunol Immunother. Nov. 8, 2008.
Thurner et al., J. Exp. Med. 190: 1669-1678 (1999).
Tjoa, Semin. Surg. Oncol. 18: 80-87 (2000).
Todo et al., Proc. Natl. Acad. Sci. USA 98: 6396-6401 (2001).
Varghese, Cancer Gene Therapy 9: 967-978 (2002).
Wroblewski et al., Lung Cancer 33: 181 (2001).
Yu et al., Cancer Res. 64(14) : 4973-4979 (2004).
Yu et al., Viral Immunol. 21(4): 435-42 (2008).
Asavaroengchai et al., Proc Natl Acad Sci USA, 99:931-936 (2002).
Eggert et al., Cancer Res, 59:3340-3345 (1999).
Fields et al., Proc Natl Acad Sci USA, 95:9482-9487 (1998).
Morse et al., Cancer Res, 59:56-58 (1999).
Steinman et al., Nature, 449:419-426 (2007).
Steinman, Nature Med, 13:1155-1159 (2007).

* cited by examiner

*Primary Examiner* — Ali R. Salimi
(74) *Attorney, Agent, or Firm* — Nixon Peabody LLP

(57) ABSTRACT

Method of stimulating an immune response (e.g., to treat cancer) include administering to a subject a composition including dendritic cells incubated with (i) oHSV-infected tumor cells or a composition derived therefrom, or (ii) tumor cells plus oHSV, as well as methods of preparing such compositions, are described.

4 Claims, 11 Drawing Sheets
(11 of 11 Drawing Sheet(s) Filed in Color)

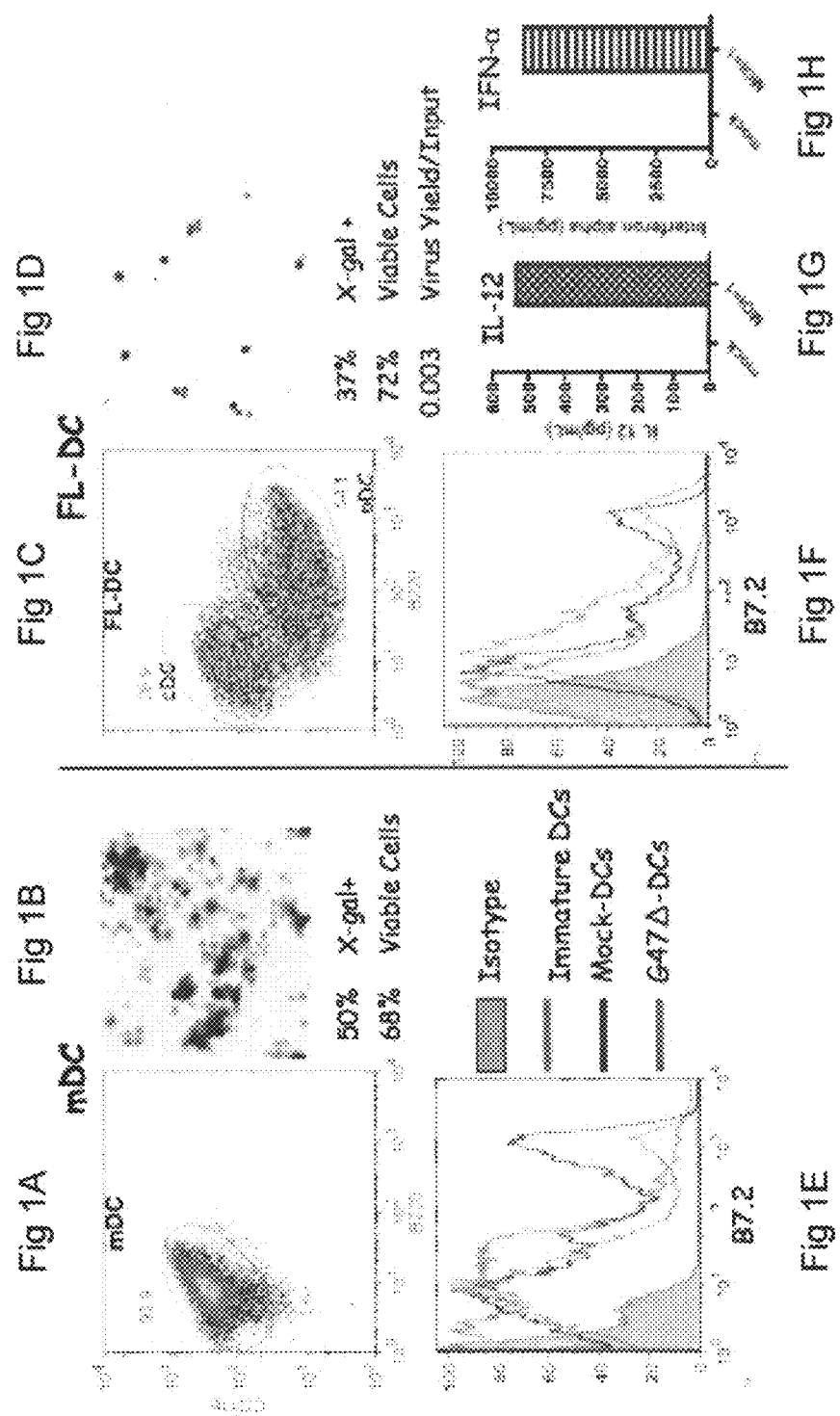

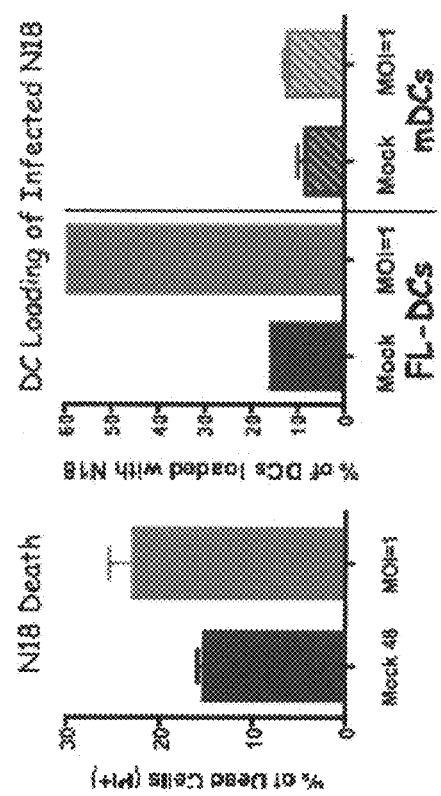

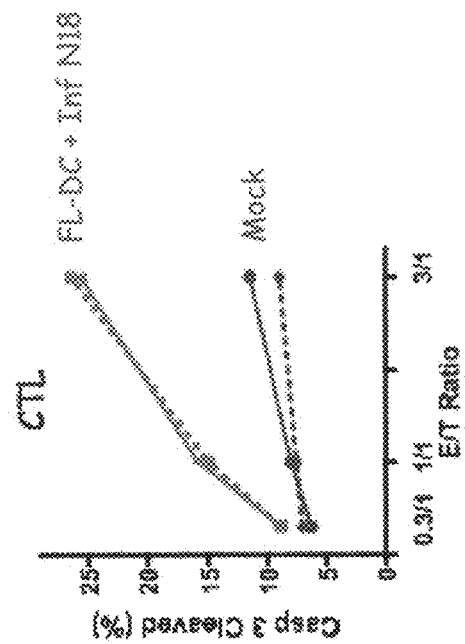
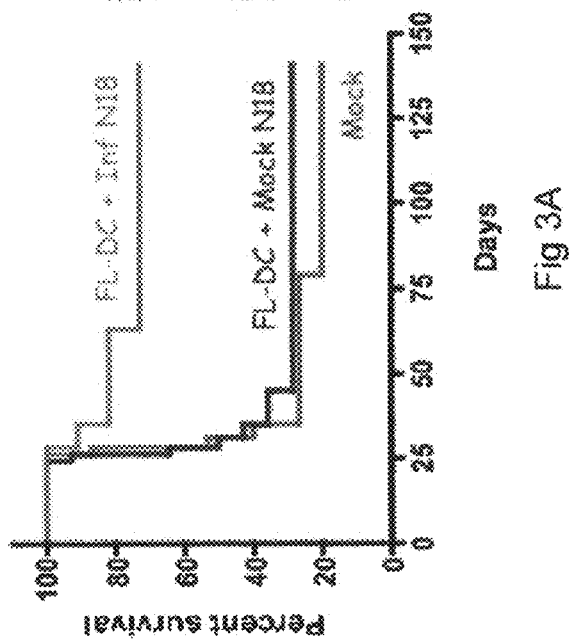
Fig 3B
Fig 3A

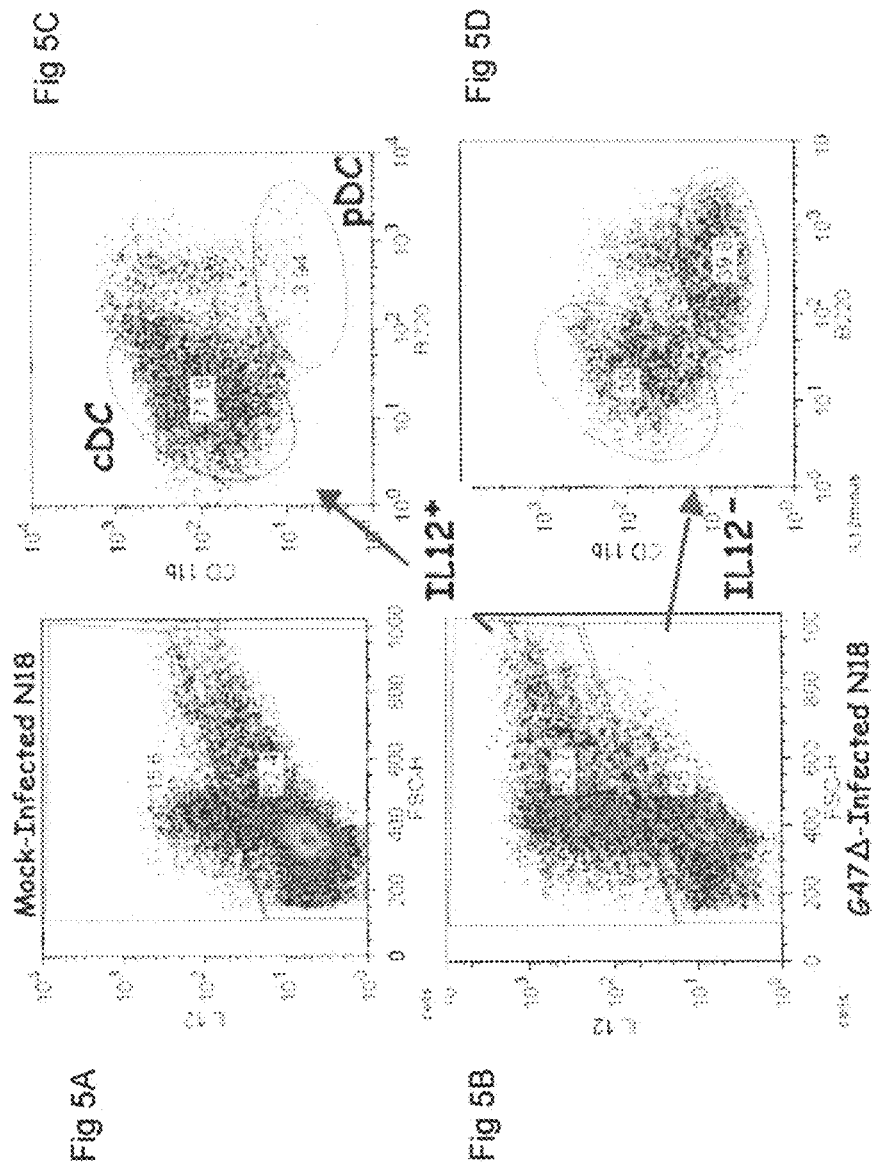

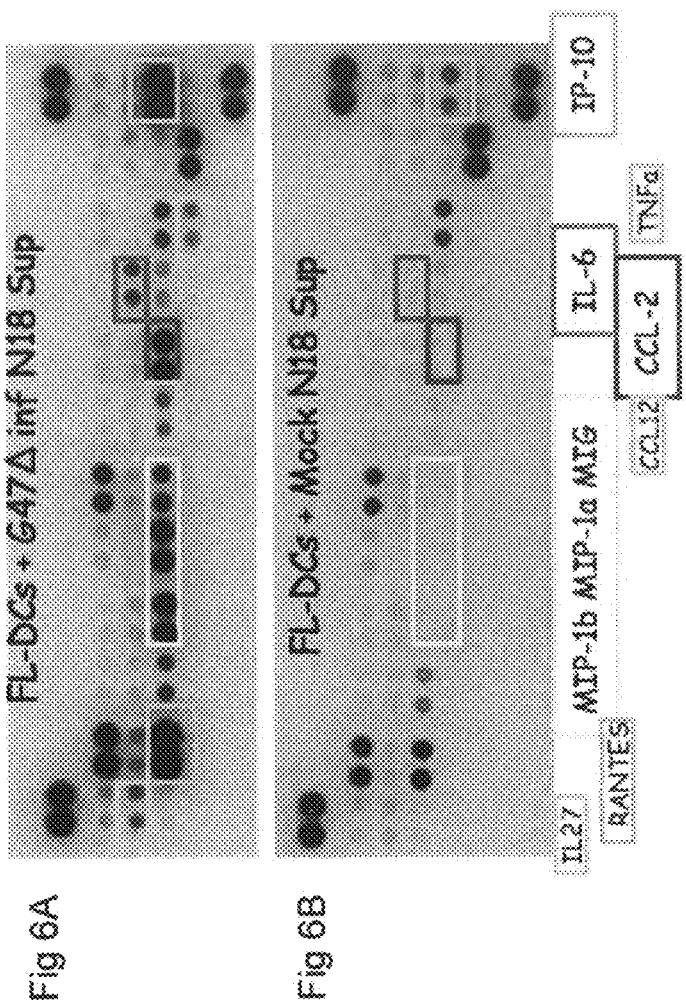

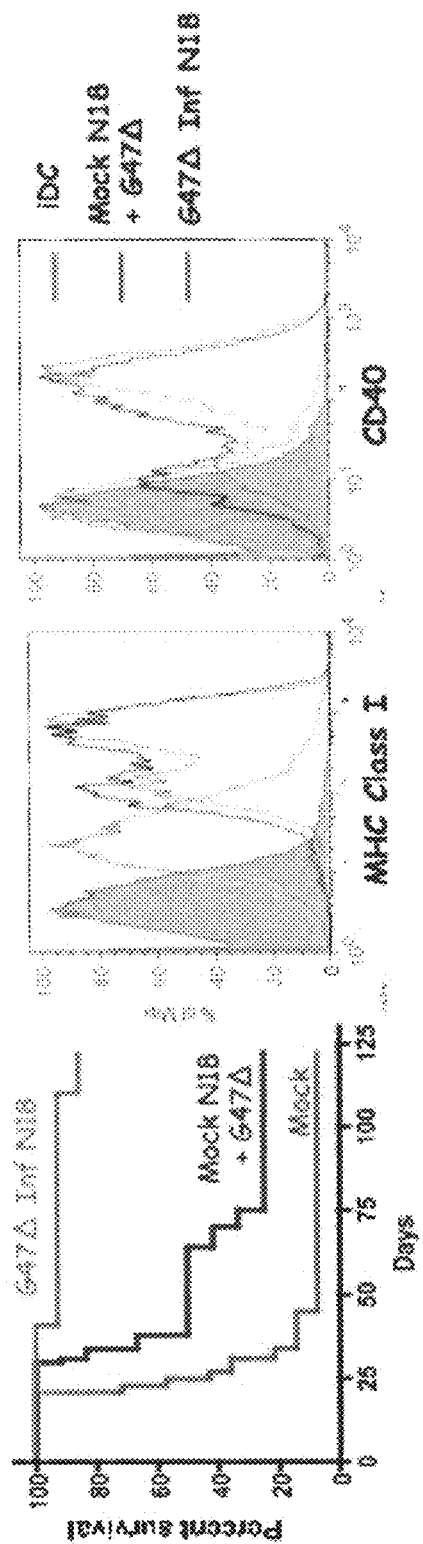

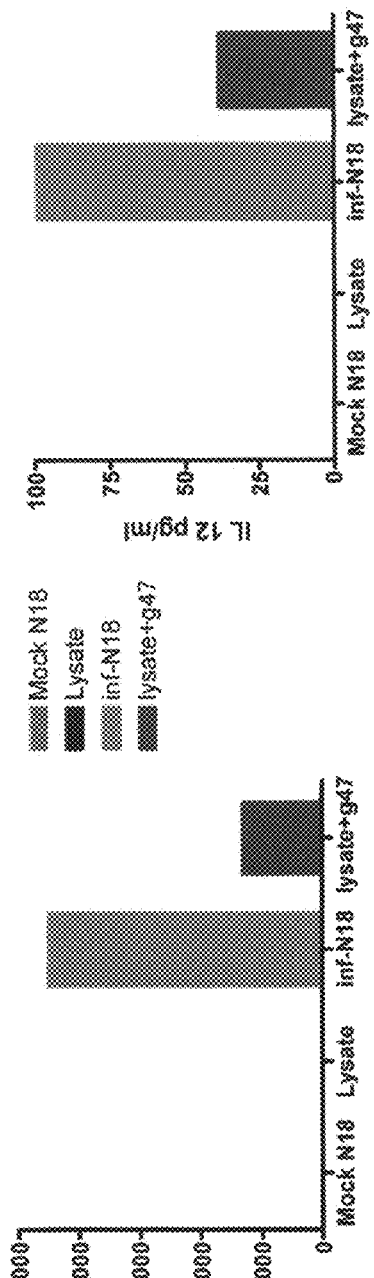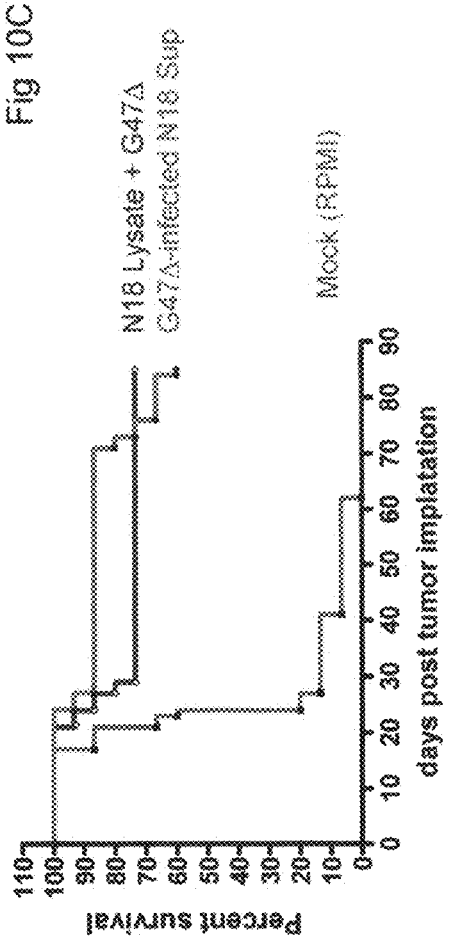

ONCOLYTIC HERPES SIMPLEX VIRUS IMMUNOTHERAPY IN THE TREATMENT OF BRAIN CANCER

CROSS-REFERENCE TO RELATED APPLICATIONS

This application claims the benefit of priority to U.S. Provisional Patent Application Ser. No. 61/123,102, filed on Apr. 4, 2008, the entire contents of which are incorporated herein by reference.

FEDERALLY SPONSORED RESEARCH OR DEVELOPMENT

This invention was made with Government support under Grant No. RO1 NS03267 awarded by the National Institutes of Health. The Government has certain rights in the invention.

BACKGROUND

A number of strategies involving the use of dendritic cells (DC) for inducing specific anti-tumor immune responses are being investigated. The use of DC "loaded" with dead cancer cells in vaccine (immunotherapy) approaches has been described in both experimental and clinical settings (see, e.g., Fields et al., Proc Natl Acad Sci USA 95:9482 (1998); Asavaroengchai et al., Proc Natl Acad Sci USA 99:931 (2002); Chang et al., Clin Cancer Res 8:1021 (2002); Geiger et al., Cancer Res 61:8513 (2001)) and others (Eggert et al., Cancer Res 59:3340 (1999); Morse et al., Cancer Res 59:56 (1999); Steinman et al., Nature 449:419 (2007); Steinman, Nature Med 13:1155 (2007)). DC pulsed with tumor-associated antigen(s) in the form of dead tumor cells (denoted TP-DC) can elicit specific T cell proliferation and CTL reactivity, and have shown efficacy in protecting naive mice from tumor challenge and in reducing the growth of tumors in vivo.

SUMMARY

This invention is based, inter alia, on the discovery that oncolytic herpes simplex virus (oHSV)-infected tumor cells can be used as a source of antigen for dendritic cells to prepare a cell vaccine (i.e., an immunomodulatory composition, e.g., an immunostimulatory composition) for treatment of cancer. The invention is also based, inter alia, on the discovery that oHSV does not interfere with the maturation of a mixed population of conventional and plasmacytoid DCs.

The invention is also based, inter alia, on the discovery that oHSV is able to act as an adjuvant and stimulate a mixed population of conventional and plasmacytoid DCs to use uninfected tumor cells as a source of antigen to prepare a vaccine for the treatment of cancer. Immunization of animals with dendritic cells pulsed with antigens from oHSV-infected tumor cells or a tumor cell lysate plus oHSV provided a significant survival benefit as compared to immunization with mock-infected tumor cells.

Accordingly, this application provides methods and compositions for cancer vaccines. New vaccines that target tumor cells can provide for greater therapeutic and/or prophylactic effect, particularly in cancers that are resistant to conventional treatments.

In one aspect, this application provides methods of treating a cancer in a subject. The methods include infecting (e.g., ex vivo) a tumor cell, e.g., a cell from a brain tumor, e.g., a glioma cell or a neuroblastoma cell, with an oncolytic herpes simplex virus (oHSV), to produce an oHSV-infected tumor cell; contacting a population of dendritic cells with the oHSV-infected tumor cell or a composition derived therefrom (e.g., a supernatant, conditioned medium, eluate, or lysate thereof), to produce a population comprising mature dendritic cells; and administering to a subject a composition comprising the mature dendritic cells, thereby treating the cancer in the subject.

In another aspect, this application provides methods of treating a cancer in a subject. The methods include contacting a population of dendritic cells with either or both of (i) an oHSV-infected tumor cell or a composition derived therefrom (e.g., a supernatant, conditioned medium, eluate, or lysate thereof) or (ii) a composition derived from a tumor cell, e.g., tumor cell lysate, plus oHSV (e.g., less than 1 plaque forming unit per 10 cells (MOI=0.1)), to produce a population comprising mature dendritic cells and administering to a subject a composition comprising the mature dendritic cells, thereby treating the cancer in the subject.

In a further aspect, this application provides methods of preparing a cancer vaccine. The methods include obtaining a population of dendritic cells and contacting the dendritic cells with (i) an oHSV-infected tumor cell or a composition derived therefrom (e.g., a supernatant, conditioned medium, eluate, or lysate thereof), and/or (ii) a composition derived from a tumor cell, e.g., tumor cell lysate, plus oHSV (e.g., less than 1 plaque forming unit per 10 cells (MOI=0.1)), thereby preparing a cancer vaccine.

In some embodiments, the population of dendritic cells comprises myeloid dendritic cells, plasmacytoid dendritic cells, conventional dendritic cells, or a mixture of plasmacytoid dendritic cells and conventional dendritic cells. In some embodiments, the population of dendritic cells is made by culturing bone marrow progenitors in the presence of Flt-3 ligand. In some embodiments, the population of dendritic cells comprises cells made by culturing mononuclear cells (e.g., monocytes) in the presence of Flt-3 ligand. In some embodiments, the population of dendritic cells is isolated. In some embodiments, the population of dendritic cells comprises dendritic cells autologous to or allogeneic to a subject.

In some embodiments, the oHSV is an oHSV-1, e.g., G207, or an oHSV derived from G207 (e.g., G47Δ). In some embodiments, the oHSV expresses an immunomodulatory transgene, e.g., Flt-3 ligand, CCL17, IL-18, HMGB1, or calreticulin.

In some embodiments, the dose of HSV used is less than 1 plaque forming unit per 10 cells (MOI=0.1)), e.g., about 0.1-0.001 MOI, or about 0.1-0.01 MOI.

In some embodiments, the tumor cell is an isolated tumor cell. In some embodiments, the oHSV-infected tumor cell is from a brain tumor, e.g., a glioma cell or a neuroblastoma cell.

In another aspect, this application provides methods of preparing a cell vaccine for treating a cancer. The methods include obtaining mononuclear cells (e.g., monocytes) from a subject; culturing the mononuclear cells in vitro under conditions in which the mononuclear cells differentiate into antigen presenting cells; isolating a tumor cell from the subject; infecting a tumor cell (e.g., ex vivo) with an oncolytic herpes simplex virus (oHSV) to produce an oHSV-infected tumor cell; and culturing the antigen presenting cells in the presence of the oHSV-infected tumor cell or a composition derived therefrom, thereby preparing a cell vaccine. In some embodiments, tumor cells or compositions derived therefrom, e.g., supernatants or lysates, are mixed with oHSV ((e.g., less than 1 plaque forming unit per 10 cells (MOI=0.1))) and cultured with antigen presenting cells. In some embodiments, the antigen presenting cells are dendritic cells (e.g., myeloid dendritic cells, plamsacytoid dendritic cells, conventional dendritic cells, or plasmacytoid dendritic cells and conventional dendritic cells). In embodiments in which the antigen presenting cells are cultured in the presence of whole tumor cells, the methods further comprise irradiating the tumor cells. In some embodiments, the conditions in which the mononuclear cells differentiate into antigen presenting cells comprise culturing the cells in the presence of Flt-3 ligand or GM-CSF. In some embodiments, the oHSV-infected tumor cell is from a brain cancer, e.g., a glioma cell or a neuroblastoma cell. In some embodiments, the oHSV is an oHSV-1, G207, or an oHSV derived from G207 (e.g., G47Δ). In some embodiments, the oHSV expresses an immunomodulatory (e.g., immunostimulatory) transgene, e.g., Flt-3 ligand, CCL17, IL-18, HMGB1, or calreticulin. In some embodiments, the dose of HSV used is less than 1 plaque forming unit per 10 cells (MOI=0.1)), e.g., about 0.1-0.001 MOI, or about 0.1-0.01 MOI. In some embodiments, the methods also include administering the cell vaccine to the subject.

In a further aspect, this application provides methods of treating a subject that include administering to the subject a therapeutically effective amount of a cell vaccine prepared by a method described herein.

In some embodiments, the subject is a non-human animal (e.g., a mammal) or a human. In some embodiments, the route of administration is subcutaneous, intradermal, or subdermal.

In another aspect, this application provides cell vaccines prepared by a method described herein.

In a further aspect, this application provides kits for preparing a cell vaccine that include one or more of an oHSV; a tumor cell infected with an oHSV; a composition derived from a tumor cell infected with an oHSV (e.g., a supernatant, conditioned medium, eluate, or lysate thereof); a composition derived from a tumor cell, e.g., tumor cell lysate and oHSV; an antigen presenting cell; an Flt-3 ligand; and GM-CSF. In some embodiments, the oHSV is an oHSV-1, G207, or an oHSV derived from G207 (e.g., G47Δ). In some embodiments, the oHSV expresses an immunomodulatory (e.g., immunostimulatory) transgene, e.g., Flt-3 ligand, HMBG1, calreticulin, GITR ligand, interleukin-12, interleukin-15, interleukin-18, or CCL17. In some embodiments, the oHSV-infected tumor cell is a brain cancer cell, e.g., a glioma cell or a neuroblastoma cell. In some embodiments, the antigen presenting cell is a dendritic cell (e.g., a myeloid dendritic cell, a plasmacytoid dendritic cell, or a conventional dendritic cell). In some embodiments, the dendritic cell is part of a population of dendritic cells, e.g., including plasmacytoid dendritic cells and conventional dendritic cells.

In some embodiments in which immunogenic compositions comprising dendritic cells that have been contacted with oHSV-infected, uninfected or mock-infected tumor cells, are made or used, the tumor cells are irradiated, e.g., prior to being contacted with the DCs.

This application also provides immunogenic compositions that include an oHSV-infected tumor cell or a composition derived therefrom (e.g., a supernatant, conditioned medium, eluate, or lysate thereof).

"Stem-like" or "stem," as used herein refers to cells that are able to self renew from a single clone, differentiate into terminal cell types, and be serially transplantable in immunodeficient animals.

"Treatment" and "treating," as used herein refer to both therapeutic treatment and prophylactic or preventative measures, wherein the object is to prevent or slow down (lessen) the targeted pathologic condition or disorder even if the treatment is ultimately unsuccessful. Those in need of treatment include those already diagnosed as having the disorder as well as those prone to have the disorder or those in whom the disorder is to be prevented. For example, in tumor (e.g., cancer) treatment, a therapeutic agent may directly decrease the pathology of tumor cells, or render the tumor cells more susceptible to treatment by other therapeutic agents or by the subject's own immune system.

"Tumor," as used herein refers to all neoplastic cell growth and proliferation, whether malignant or benign, and all pre-cancerous and cancerous cells and tissues.

One advantage of the methods described herein is the elimination of the requirement of identification of tumor-associated antigens (TAAs) as all antigenic epitopes expressed by the tumor cells are exploited. Further, the infection and/or cell killing by the virus provides signals that facilitate the maturation and activation of DCs. Where supernatant of infected tumor cells is employed, the supernatant provides a convenient reagent to handle and stock. Also, the use of a mixed population of conventional and plasmacytoid DCs avoids potential problems with virus interference with DC maturation.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A is a scatter plot of myeloid dendritic cells (mDCs) characterized by flow cytometric analysis using anti-CD11b-FITC and anti-B220-APC.

FIG. 1B is a micrograph of G47Δ-infected mDCs stained with Xgal to determine the number of infected cells. Percentages of X-gal$^+$ and viable (non-propidium iodide staining) cells are indicated below the figure.

FIG. 1C is a scatter plot of Flt-3 ligand differentiated dendritic cells (FL-DCs) characterized by flow cytometric analysis using anti-CD11b-FITC and anti-B220-APC.

FIG. 1D is a micrograph of G47Δ-infected FL-DCs stained with Xgal to determine the number of infected cells. Percentages of X-gal$^+$ and viable (non-propidium iodide staining) cells and virus yield are indicated below the figure.

FIGS. 1E and 1F are histograms of B7.2 expression on immature DCs, mock-infected DCs (Mock-DCs), and DCs infected with G47Δ using either mDCs (1E) or FL-DCs (1F). Isotype controls are indicated for reference.

FIGS. 1G and 1H are bar graphs depicting IL-12 (1G) and IFN-A (1H) expression of mock-infected and G47Δ-infected (MOI=1) FL-DCs.

FIG. 2A is a bar graph depicting the percentage of dead N18 cells at 48 hours following infection with G47Δ (MOI=1) or mock infection (Mock 48).

FIG. 2B is a bar graph depicting the percentage of FL-DCs and mDCs loaded with mock infected N18 (Mock) or G47Δ-infected N18 (MOI=1).

FIG. 3A is a line graph depicting survival of mice subcutaneously injected with N18 cells ($5 \times 10^5$ cells/mouse) after being vaccinated twice with CD11c$^+$ sorted FL-DCs ($5 \times 10^5$/mouse) loaded with G47Δ-infected N18 (FL-DC+Inf N18) or mock-infected N18 (FL-DC+Mock N18), or with RPMI medium (Mock).

FIG. 3B is a line graph depicting CTL activity as depicted by caspase 3 cleavage for CTLs incubated with FL-DC+Inf N18 and RPMI (Mock).

FIGS. 5A and 5B are scatter plots of IL-12 expression (IL-12) and forward scatter (FSC-H) for FL-DCs pulsed overnight with G47Δ-(5B) or mock-infected (5A) N18 supernatant.

FIGS. 5C and 5D are scatter plots of CD11b and B220 expression of IL-12$^+$ (5C) and IL-12$^-$ FL-DCs (5D) pulsed overnight with G47Δ-infected N18 supernatant. Percent of cDCs and pDCs are indicated in the respective ovals.

FIGS. 6A and 6B are dot blots depicting expression of chemokines/cytokines in supernatants of FL-DCs pulsed overnight with G47Δ-(6A) or mock-infected (6B) N18 supernatant. Chemokines/cytokines differentially expressed between the two cell populations (IL-27, RANTES, MIP-1b, MIP-1a, MIG, CCL12, CCL-2, IL-6, TNF-α, and IP-10) are indicated by the colored boxes.

FIG. 9A is a line graph depicting percent survival of mice vaccinated subcutaneously with FL-DCs ($5 \times 10^5$/mouse) pulsed with G47Δ-infected N18 supernatant (n=14) (G47Δ Inf N18), mock-infected N18 supernatant supplemented with G47Δ(n=12) (Mock N18+G47Δ) or RPMI (n=14) (Mock) 14 and 7 days before challenge subcutaneously with N18 cells ($5 \times 10^5$/mouse).

FIGS. 9B and 9C are histograms of MHC Class I (8B) and CD40 (8C) expression of immature DCs (iDC), DCs incubated with mock-infected N18 supernatant with G47Δ (n=12) (Mock N18+G47Δ) or G47Δ-infected N18 cells (G47Δ Inf N18). Isotype controls are indicated for reference (filled).

FIG. 10A is a bar graph depicting IFN-alpha expression by FL-DCs after pulsing with mock-infected N18 supernatant, N18 lysate, G47Δ-infected N18 supernatant, or N18 lysate+low-dose G47Δ.

FIG. 10B is a bar graph depicting IL-12 expression by FL-DCs after pulsing with mock-infected N18 supernatant, N18 lysate, G47Δ-infected N18 supernatant, or N18 lysate+low-dose G47Δ.

FIG. 10C is a line graph depicting percent survival of mice challenged with N18 tumor cells subcutaneously after vaccination with FL-DCs pulsed with G47Δ-infected N18 supernatant, N18 lysate+low-dose G47Δ (MOI=0.01), or RPMI media (Mock).

DETAILED DESCRIPTION

Figure 4A:
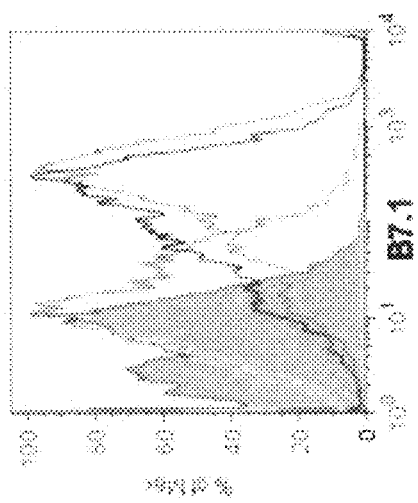
FIGS. 4A and 4B are histograms of B7.1 (4A) and CD40 (4B) expression of immature DCs (iDC), DCs incubated with G47Δ-infected N18 supernatant diluted 10-fold (+Inf Spn) or G47Δ-infected N18 cells (+Inf Cells). Isotype controls are indicated for reference (filled).

In general, the vaccines (immunogenic compositions) described herein include dendritic cells pulsed with tumor cells infected with an oncolytic herpes simplex virus (oHSV) (i.e., irradiated tumor cells), or a composition derived from a tumor cell, e.g., tumor cell lysate, plus oHSV, or with a composition derived therefrom, e.g., supernatant or lysate from the oHSV-infected tumor cells (when the composition includes tumor cells, they will be irradiated prior to administration of the compound, e.g., prior to being combined with the dendritic cells).

Tumor Cells

The population of tumor cells provides the tumor antigens. Depending on the specific tumor type to be treated in a subject, the cells can be from a solid or hematopoietic-derived tumor. Tumors can be harvested surgically from subjects. The harvested tumors can be used freshly or cryopreserved for later use. A single cell suspension can be made by a combination of mechanical and enzyme dispersion techniques. For long-term storage, cancer cells can be frozen in a liquid nitrogen freezer.

In some embodiments, the tumor cells are obtained from the subject to whom they can be delivered, i.e., autologous, or from another subject having the same type of cancer, i.e., allogeneic. In some embodiments, the tumor cells are from a cell line.

In some embodiments, the methods include obtaining a sample of a tumor in a subject to be treated using a method described herein, and detecting the presence of tumor-associated antigens (TAA) on cells of the tumor. Then, cells from a tumor in another subject, or from a combination of tumors in other subjects, can be chosen that express the same tumor-associated antigens. A number of tumor-associated antigens are known in the art, and methods for detecting them are well known. For example, several TAAs over-expressed in NSCLC cell lines have been identified. These include MAGE-1, 2, and 3, CEA, HER-2/neu, and WT-1. Characterization of 31 NSCLC lines showed that the majority tested express HER-2/neu (90%) and CEA (58%) on the cell surface. Two lung adenocarcinoma cell lines, NCI-H1944 and NCI-H2122, that together express HER-2/neu, CEA, GD-2, WT-1, and MAGE-1, -2, and -3 (Wroblewski et al., Lung Cancer 33:181 (2001)) can be used.

In some embodiments, the tumor cells are obtained from one or more cell lines made from cells of a tumor that is from the same type of cancer that the subject has, e.g., one or more human non-small cell lung cancer (NSCLC) cell lines for use in a subject who has NSCLC. Cancer cell lines are known in the art, and numerous examples are commercially available, e.g., from the American Type Culture Collection (ATCC) (Manassas, Va.), which has over 1100 different tumor cell lines from a variety of cancer types and species. For example, HPAC for pancreatic cancer, CA-HPV-10 for prostate cancer, DLD-1 for colon cancer, TOV-21G for ovarian cancer, 786-O for kidney cancer, HepG2 for liver cancer, M059K for brain cancer, 8E5 for acute lymphoblastic leukemia, 1A2 for lymphoma, NCI-H929 for myeloma.

Oncolytic Herpes Simplex Virus (oHSV)

Oncolytic herpes simplex viruses (oHSV) are known in the art and are described, for example, in Kim et al. (1999, In: Gene Therapy of Cancer, Academic Press, San Diego, Calif., pp. 235-248), and include type 1 herpes simplex viruses and type 2 herpes simplex viruses. Preferably, the oHSV is replication-selective or replication-competent, although replication-incompetent oHSV can be used in the methods, compositions, and kits described herein.

The oHSV can include an exogenous nucleic acid (i.e. it may be an oncolytic virus vector). When the oHSV comprises an exogenous nucleic acid, the nucleic acid preferably encodes an anti-oncogenic or oncolytic gene product. In some embodiments, the gene product can be, for example, one that inhibits growth or replication of only the cell infected by the virus (e.g., an antisense oligonucleotide), or it can be one that exerts a significant bystander effect upon lysis of the cell infected by the virus (e.g. thymidine kinase).

Herpes simplex 1 type viruses are among the preferred viruses, for example HSV-1 viruses that do not express functional ICP34.5 and thus exhibit significantly less neurotoxicity than their wild type counterparts. When the oHSV is a herpes simplex virus-1, it is preferably one which does not express functional ICP34.5 protein (e.g. HSV-R3616) or one of the HSV-1 viruses described in Coukos et al., Gene Ther. Mol. Biol. 3:79-89 (1998), or Varghese and Rabkin, Cancer Gene Therapy 9:967-978 (2002). Other exemplary HSV-1 viruses include 1716, R3616, and R4009. Other replication selective HSV-1 virus strains that can be used include, e.g., R47Δ (wherein genes encoding proteins ICP34.5 and ICP47 are deleted), G207 (genes encoding ICP34.5 and ribonucleotide reductase are deleted), NV1020 (genes encoding UL24, UL56 and the internal repeat are deleted), NV1023 (genes encoding UL24, UL56, ICP47 and the internal repeat are deleted), 3616-UB (genes encoding ICP34.5 and uracil DNA glycosylase are deleted), G92A (in which the albumin promoter drives transcription of the essential ICP4 gene), hrR3 (the gene encoding ribonucleotide reductase is deleted), and R7041 (Us3 gene is deleted) and HSV strains that do not express functional ICP34.5 and that express a cytokine such as interleukin-2, interleukin-4, interleukin-12, or GM-CSF.

oHSV for use in the methods and compositions described herein is not limited to one of the HSV-1 mutant strains described herein. Any replication-selective strain of a herpes simplex virus may be used. In addition to the HSV-1 mutant strains described herein, other HSV-1 mutant strains that are replication selective have been described in the art. Furthermore, HSV-2, mutant strains such as, by way of example, HSV-2 strains 2701 (RL gene deleted), Delta RR (ICP10PK gene is deleted), and FusOn-H2 (ICP10 PK gene deleted) can also be used in the methods and compositions described herein.

The oncolytic viruses useful in the present methods and compositions are, in some embodiments, replication-selective. It is understood that an oncolytic virus may be made replication-selective if replication of the virus is placed under the control of a regulator of gene expression such as, for example, the enhancer/promoter region derived from the 5'-flank of the albumin gene (e.g. see Miyatake et al., 1997, J. Virol. 71:5124-5132). By way of example, the main transcriptional unit of an HSV may be placed under transcriptional control of the tumor growth factor-beta (TGF-beta) promoter by operably linking HSV genes to the TGF-beta promoter. It is known that certain tumor cells overexpress TGF-beta, relative to non-tumor cells of the same type. Thus, an oncolytic virus wherein replication is subject to transcriptional control of the TGF-beta promoter is replication-selective, in that it is more capable of replicating in the certain tumor cells than in non-tumor cells of the same type. Similar replication-selective oncolytic viruses may be made using any regulator of gene expression which is known to selectively cause overexpression in an affected cell. The replication-selective oncolytic virus may, for example, be an HSV-1 mutant in which a gene encoding ICP34.5 is mutated or deleted.

In some embodiments, the oHSV expresses an immunomodulatory (e.g., immunostimulatory) transgene, e.g., Flt-3 ligand, HMBG1, calreticulin, GITR ligand, interleukin-12, interleukin-15, interleukin-18, or CCL17.

In a preferred embodiment, the oHSV is G47Δ. G47Δ is a third generation virus, which contains 1) a mutation of ICP6, which targets viral deletion to tumor cells, 2) a deletion of γ34.5, which encodes ICP34.5 and blocks eIF2α phosphorylation and is the major viral determinant of neuropathogenicity, and 3) an additional deletion of the ICP47 gene and US11 promoter, so that the late gene US11 is now expressed as an immediate-early gene and able to suppress the growth inhibited properties of γ 34.5 mutants. Deletion of ICP47 also abrogates HSV-1 inhibition of the transporter associated with antigen presentation and MHC class 1 downregulation (Todo et al., Proc. Natl. Acad. Sci. USA, 98:6396-6401, 2001).

Dendritic Cells (DC)

Dendritic cells (DC) are highly potent antigen-presenting cells of bone marrow origin that are integral in the stimulation of primary and secondary T- and B-cell responses. DC can be prepared from peripheral blood, umbilical cord blood, or bone marrow using methods known in the art, e.g., as described in Bernhard et al., Cancer Res, 55:1099 (1995); Chang et al., Clin Cancer Res 8:1021 (2002); and Geiger et al., Cancer Res 61:8513 (2001) (see also Example 6 herein). In some embodiments, the DC are obtained from CD34+ hematopoietic progenitor cells, e.g., derived from bone marrow or cord blood, or granulocyte-macrophage colony stimulating factor-mobilized peripheral blood, e.g., as described in Bernhard et al., Cancer Res, 55:1099 (1995); thus the methods described herein can include a step of obtaining a sample comprising bone marrow or peripheral blood from a subject, and preparing an enriched population of DC therefrom using known methods. Optionally, an effective amount of a progenitor cell mobilizing agent, e.g., G-CSF, can be administered to the subject before the sample of blood is obtained, e.g., as described in Bernhard et al., Cancer Res, 55:1099 (1995). DC can also be derived and expanded from CD34+ hematopoietic progenitor cells, e.g., from umbilical cord blood or bone marrow, by inducing dendritic cell differentiation and proliferation with GM-CSF (see, e.g., Inaba et al., Proc. Natl. Acad. Sci. USA, 90:3038-42, 1993), GM-CSF plus TNF-alpha (see, e.g., Caux et al., Nature (Lond.) 360: 258-261 (1992)), GM-CSF plus IL4 (Romani, N. et al. J. Exp. Med. 180, 83-93 (1994)), or Flt3 ligand (see, e.g., Naik et al., Nature Immunol., 8:1217-26, 2007). In some preferred embodiments, the DC are obtained from CD14+ monocytes, e.g., as described in Chang et al., Clin Cancer Res 8:1021 (2002); and Geiger et al., Cancer Res 61:8513 (2001) (see also Example 6 herein). Conditions for maturation of DCs in vitro from PBMCs are described in Table 1 of Conti and Gessani, Immunobiology 213:859-70 (2008).

Myeloid or conventional dendritic cells are either murine CD8-alpha(+) cells that express high levels of CD11c (Shortman and Liu, Nature Rev. Immunol. 2:151-161 (2002)), or human cells that express CD11c and BDCA1 (also named CD1c) or BDCA3 (MacDonald, et al Blood. 100 (13), 4512-4520 (2602); Narbutt et al., Cell. Mol. Biol. Lett., 9:497-509 (2004); Piccioli et al., Blood. 109(12):5371-9 (2007)), or equivalent cells of other species.

Plasmacytoid dendritic cells (Grouard et al., J. Exp. Med., 185:1101-11 (1997); Siegal et al., Science, 284:1835-37 (1999); Cella et al., Nat. Med. 5: 919-923 (1999); Dzionek, A., et al., J. Exp. Med. 194: 1823-1834 (2001).) are derived from CD34(+) cells committed to the lymphoid lineage. These cells do not express CD 11c, are negative for myeloid markers, express high levels of CD45RA, IL3 receptors (CD123) and BDCA2, and have been shown to express the BST-2 antigen. These cells were originally identified as natural IFN-producing cells or IFN-producing cells (Fitzgerald-Bocarsly et al., J. Leukocyte Biol., 43:323-334, 1988; Sandberg et al., Scand. J. Immunol., 29:651-658, 1989).

The population of enriched derived DC will have at least about 50% (i.e., the population of cells includes at least about 50%) DC, or at least 60%, 70%, 80%, 90%, or more DC. Thus a population of cells that is at least about 50% DC is considered to be "enriched," as used herein As one of skill in the art would appreciate, the presence of other cells, e.g., other blood cells, in the preparation does not generally affect the therapeutic efficacy or usefulness of the DC. As used herein, "about" indicates a value plus or minus up to 5%.

In general, the methods described herein will use DC obtained from a subject to whom they will be administered, i.e., autologous DC. In some embodiments, DC from a very closely matched donor may be used, e.g., a donor who is so closely matched that no immune suppression, or only very minimal suppression, would be needed.

Preparing a Cell-Based Vaccine Composition

In some embodiments, the tumor cells are infected by oHSV using methods known in the art, e.g., as described herein. In some embodiments, the dose of HSV used is less than 10 plaque forming unit per tumor cells (MOI=10)), e.g., about 00.1-10 MOI, or about 0.1-1 MOI, or about 1 MOI.

In some embodiments, the composition includes a composition derived from mock-infected or uninfected tumor cells, e.g., tumor cell lysate, dendritic cells, and G47Δ, and preparing the vaccine can simply include mixing the lysate, dendritic cells, and oHSV. In some embodiments, the dose of HSV used is less than 1 plaque forming unit per 10 dendritic cells (MOI=0.1)), e.g., about 0.1-0.001 MOI, or about 0.1-0.01 MOI, or about 0.1 MOI.

In some embodiments, additional ingredients can be added to the reconstituted vaccine, e.g., adjuvants. In embodiments where whole tumor cells are used, the cells will generally be irradiated or otherwise treated to reduce cell viability before use, e.g., irradiated with 15 Gy, e.g., before being combined with the dendritic or antigen presenting cells.

In general, before treatment, the tumor cells, compositions derived therefrom, and/or dendritic cells are thawed (if frozen), washed (e.g., with media or physiologically acceptable buffer), and combined to create a vaccine composition. The exact ratio of cells is not crucial, and optimal ratios can be determined based on animal and in vitro studies; for most purposes, roughly equivalent numbers of cells will be sufficient.

Methods of Treating Cancer

The methods described herein include methods for the treatment of cancer. Generally, the methods include administering a therapeutically effective amount of the vaccine compositions described herein, to a subject who is in need of, or who has been determined to be in need of, such treatment. As used herein, the term "treat" means to decrease the growth or growth rate of a tumor, prevent or delay re-growth of a tumor, e.g., a tumor that was debulked, e.g., surgically debulked, or treated using radiation or chemotherapy, or to decrease the size of a tumor. The methods of treatment include initiating or enhancing an anti-tumor immune response in the subject.

Dendritic cells (DC) pulsed with a tumor antigen have been shown to elicit specific tumor-reactive T cells in preclinical and clinical studies. A number of Phase I and early Phase II clinical trials have shown that DC presenting tumor-associated antigens can lead to partial or complete regression of tumors (see, e.g., Hsu et al., Nat. Med., 2: 52-58 (1996) (B-cell lymphoma); Nestle et al., Nat. Med., 4: 328-332 (1998) (melanoma); Thurner et al., J. Exp. Med., 190: 1669-1678, (1999) (advanced stage 1V melanoma); Lim and Bailey-Wood, Int. J. Cancer, 83: 215-222 (1999) (multiple myeloma); Tjoa and Murphy, Semin. Surg. Oncol., 18: 80-87 (2000) (prostate cancer); Geiger et al., Lancet, 356: 1163-1165 (2000) (solid tumors in children); Chang et al., Clin Cancer Res 8:1021 (2002) (various stage 1V solid malignancies); and Geiger et al., Cancer Res 61:8513 (2001) (pediatric solid tumor patients); Yu et al., Cancer Res. 64(14):4973-4979 (2004)(malignant glioma); Lopez et al., J Clin Oncol. 27(6):945-52 (2009), Epub 2009 Jan. 12 (melanoma); Lepisto et al., J Clin Oncol. 27(6):945-52 (2009, Epub 2009 Jan. 12 (pancreatic and biliary tumors); Yu et al., Viral Immunol. 21(4):435-42 (2008) (ovarian cancer); Burgdorf et al., Oncol Rep. 20(6):1305-11 (2008) (colorectal cancer); Schuetz et al., Cancer Immunol Immunother. 2008 Nov. 8 (breast cancer); Palmer et al., Hepatology. 49(1):124-32 (2009) (hepatocellular carcinoma); Mackell et al., Clin Cancer Res. 14(15):4850-8 (2008) (pediatric Sarcoma/Ewing's sarcoma). See also Weber and Schulz, Princ. Pract. Biol. Ther. Cancer, 1: 2-11, 2000; Palucka et al., J. Immunother. 31(9):793-805 (2008); Palucka et al., Immunol Rev. 220:129-50 (2007). The methods described herein can be used to treat any of these cancers, as well as any cancer that presents an antigen recognizable by the immune system.

As used herein, the term "cancer" refers to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. In general, a cancer will be associated with the presence of one or more tumors, i.e., abnormal cell masses. The term "tumor" is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth.

Tumors include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, hepatocellular cancer, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

Additional examples of cancers that can be treated using the methods and compositions described herein include brain and nervous system cancers, including, but not limited to, gliomas, glioblastomas, glioblastoma multiforme (GBM), oligodendrogliomas, primitive neuroectodermal tumors, low, mid and high grade astrocytomas, ependymomas (e.g., myxopapillary ependymoma papillary ependymoma, subependymoma, anaplastic ependymoma), oligodendrogliomas, medulloblastomas, meningiomas, pituitary adenomas, neuroblastomas, neurofibromas, malignant peripheral nerve sheath tumors, schwannomas, and craniopharyngiomas. In some embodiments, cancers treated by the methods described herein include those that are particularly immunogenic, e.g., neuroblastoma, melanoma, and renal cell cancer.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. For example, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The vaccines described herein can be administered to a subject, e.g., a cancer patient, by a variety of routes. For example, subcutaneous, intradermal, or subdermal.

Data obtained from in vitro cell cultures and animal models can be used to project an efficacious dose regimen in humans, including dose and frequency. A projected optimal human efficacious dose regimen can be selected and further tested in clinical trials.

In general, efficacious dose regimen (dose and frequency) ranges for the vaccine include amounts sufficient to treat cancers. Such doses include, e.g., about $1\times10^5$ dendritic cells to $1\times10^8$ dendritic cells per dose, e.g., about $0.5\times10^6$ dendritic cells to $1\times10^7$ dendritic cells per dose, e.g., about $1\times10^6$ dendritic cells per dose. These numbers are general guidelines, which one of skill in the art can use to determine optimal dosing. Suitable dose frequencies include, e.g., every 2 weeks for 3 doses, every week for 12 doses; or every other week for four doses. In some embodiments, a dose is administered every few days for a week (for 2-3 doses in a week), and then additional doses are administered once a month or every 2-3 weeks. The treatment can also be resumed after a certain period if needed. The dose regimen, including both dose and frequency, can be adjusted based on the genetic, demographic, and pathophysiological characteristics of the subject, and disease status. For example, the age, sex, and weight of a subject to be treated, and the type or severity of the subject's cancer. Other factors that can affect the dose regimen include the general health of the subject, other disorders concurrently or previously affecting the subject, and other concurrent treatments.

The dose of the vaccine can be flat (e.g., in cells/dose) or individualized (e.g., in cells/kg or cells/$m^2$ dose) based on the safety and efficacy of the treatment and the condition of the subject. The dose and frequency can also be further individualized based on the tumor burden of the subject (e.g., in cells/tumor size, cells/kg/tumor size or cells/$m^2$/tumor size dose). It should also be understood that a specific dose regimen for any particular subject can depend upon the judgment of the treating medical practitioner. In determining the effective amount of the cells to be administered, the treating medical practitioner can evaluate factors such as adverse events, and/or the progression of the disease.

Combination Therapy

The vaccine compositions described herein can be used as a monotherapy or as part of a multi-modal therapeutic regimen. The vaccine can be administered to a subject in combination with other treatment modalities with different mechanisms of action, for example, surgery, radiation, cytotoxic chemotherapy (e.g., cyclophosphamide, 5-fluorouracil, cisplatin, gemcitabine), targeted biologic agents (e.g., monoclonal antibodies, fusion proteins, tyrosine kinase inhibitors), and immune modulators (e.g., cytokines and/or CTLA-4, PDL-1, PD-1 antibodies). These combination therapies can have additive or synergistic effects. The vaccine can also be used in combination with other cancer vaccines that carry different tumor-associated antigens. The various treatments can be administered concurrently or sequentially (e.g., before or after treatment using a method described herein). For example, one treatment can be given first, followed by the initiation of administration of other treatments after some time. A previous therapy can be maintained until another treatment or treatments have effect or reach an efficacious level.

In one example, a surgical treatment method is administered first, to remove as much of the tumor tissue as possible, and then one or more doses of the vaccine as described herein are administered. In another example, one or more doses of the vaccine as described herein are administered prior to administration of a dose of cytotoxic radiation or chemotherapy, e.g., to sensitize the tumor cells to the radiation or chemotherapy and thereby enhance the effect of the radiation or chemotherapy. See, e.g., Antonia et al., Clin. Cancer Res. 12(3):878-887 (2006); Schlom et al., Clin. Cancer Res. 13(13):3776-3781 (2007) Thus, the methods described herein can include first administering one or more doses of the vaccine as described herein, followed by one or more doses of radiation or chemotherapy.

Evaluating Subjects Pre-Treatment and Post-Treatment

Prior to initiation of the vaccine treatment, subjects can be tested for the need of treatment. The clinical signs and symptoms of cancer, which are known in the art, can be an indicator of treatment need although an earlier predictor of treatment is more desirable. The dose regimen of the vaccine can be adjusted based on the severity of clinical signs and symptoms of cancer.

Following administration of the vaccine, the efficacy and safety of the treatment can be assessed in several ways, indirectly or directly. The parameters, including levels of biomarkers (for example, immune responses such as increased IFN-γ production), immune assays (for example, lymphocyte phenotypic and functional assays), clinical signs and symptoms (for example, tumor response (e.g., growth and/or overall size) by imaging, progression-free survival or overall survival), and/or adverse events, can be evaluated over time in the same subject. The parameters can also be compared between actively treated subjects and placebo subjects at the same time points. The parameters can be the absolute values or the relative changes from the baseline in the same subject or compared to placebo subjects. The levels of biomarkers associated with cancer and treatment in subject samples can be monitored before and after treatment. The number and/or severity of clinical signs and symptoms in a subject can be compared before and after treatment, including long-term follow-up after the last dose. The adverse events can also be monitored and compared between active and placebo groups or between baseline and post-treatment in the active group. For example, a subject (e.g., a cancer patient) can have an initial assessment of the severity of his or her disorder (e.g., the number or severity of one or more symptoms of cancer), receive vaccine treatment as a monotherapy or part of a combination therapy, and then be assessed subsequently to the treatment at various time points (e.g., at one day, one week, one month, three months, six months, one year, two years and three years).

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

HSV Infection of DC Subsets

The susceptibility and consequences of HSV infection of dendritic cells (DCs) were examined. There have been reports describing wild-type HSV infection of DCs, mostly human and of monocyte-derived DCs (moDCs) (Kobelt et al., Curr. Top. Microbiol. Immunol., 276:145-161, 2003). The typical response to HSV infection is interference in DC maturation (Salio et al., Eur. J. Immunol., 29:3245-53, 1999; Novak and Peng, Clin. Exp. Immunol., 142:405-410, 2005). However, responses to oHSV have not been examined. Monocytes from mouse bone marrow were cultured under two differentiation conditions: one with GM-CSF, which generates myeloid DCs (mDCs) and the other with Flt3-ligand, which generates a mixed population (FL-DCs) consisting of conventional (cDCs) and plasmacytoid (pDCs) DCs (FIGS. 1A-1B). Bone marrow (BM) progenitors obtained from A/J mice were cultured at a density of $10^6$ cells/ml in RPMI supplemented with 10% heat-inactivated fetal calf serum (FCS), 1 mM nonessential amino acids, 10 mM Hepes, 1 mM Sodium Pyruvate, 50 mM β-mercaptoethanol (β-ME). Immature FL-DCs were obtained after 8 days of culture with 20 ng/mL of murine Flt3-ligand (R&D). Immature mDCs were cultured in media supplemented with 10 ng/mL of murine GM-CSF (Sigma). Three days later, floating cells were removed and fresh medium with 10 ng/mL of GM-CSF added, after 7 days mDCs were harvested. DCs in Flt3-ligand and GM-CSF supplemented medium were enriched using CD11c microbeads (Miltenyi Biotech) following the manufacturer's instruction. DC purity was >90%. mDCs, pDCs, and cDCs were characterized by flow cytometric analysis using anti-CD11b-FITC, anti-B220-APC (BD) (FIGS. 1A, 1C). DCs infected at a multiplicity of infection (MOI) of 1 PFU/cell by G47Δ for 90 minutes, were washed and seeded at $10^6$ cells/ml in 6-well plates in medium containing either GM-CSF or Flt3-ligand. Twenty-four hours post infection, the percent of infected cells was determined by x-gal staining, percent of viable cells was determined by propidium iodide staining using Nucleocounter system (New Brunswick), and virus yield by plaque assay (Todo et al., Proc. Natl. Acad. Sci. USA, 98:6396-6401, 2001) (FIGS. 1B, 1D). DC phenotypes were analyzed by fluorescence activated cell sorting (FACS) (FIGS. 1E, 1F), and IL-12 (FIG. 1G) and IFN-α (FIG. 1H) levels in the supernatant of infected FL-DCs were determined by ELISA (R&D). Both immature mDCs and FL-DCs are susceptible to oHSV infection. As has been described before with wild-type HSVs, oHSV infection of mDCs inhibits maturation. However, FL-DC maturation and cytokine secretion are not affected by oHSV infection, a novel finding.

Example 2

DC Loading of Infected Tumor Cells and Maturation

Next, whether G47Δ-infected N18 cells could be loaded by DCs was examined. Infected N18 cells were labeled with a fluorescent dye (CFSE) and mixed with immature mDCs or FL-DCs. There was not a large difference in N18 viability, with or without G47Δ infection (p=0.03, t-test; FIG. 2A). To determine loading of DCs, N18 cells labeled with CFSE reagent (0.2 µM) were seeded in 6-well plate and infected with G47Δ at a MOI of 1 or mock infected. Two days later, N18 cells were scraped and incubated with sorted mDCs or FL-DCs. N18 ($10^6$) were incubated with DCs ($3\times10^6$) overnight, harvested, labeled with anti-CD11c-PE and analyzed by flow cytometry. The percent of DCs loaded (percent of CFSE$^+$ CD11c$^+$ double-positive DCs among all CD11c$^+$) are shown in FIG. 2B. FL-DCs took up G47Δ-infected N18 very efficiently, but not mock-infected N18, and mDCs loaded both poorly. G47Δ-infected pulsed FL-DCs were highly matured based on analysis by FACS for surface markers MHC class I and II, CD40, co-stimulatory molecules B7.1 and B7.2, and chemokine receptor CCL7).

Since FL-DCs pulsed with G47Δ-infected N18 cells were observed to mature in vitro, we examined whether these pulsed DCs could protect mice from a lethal tumor challenge. Fourteen and 7 days before subcutaneous injection of N18 ($5\times10^5$ cells/mouse), A/J mice were injected into the scapular subcutaneously with CD11c$^+$ sorted FL-DCs ($5\times10^5$/mouse) loaded with G47Δ-infected N18 or mock-infected N18, or with RPMI medium. N18 were irradiated (15Gy) prior to pulsing. Vaccination with G47Δ-infected N18 pulsed FL-DCs caused a significant prolongation in median survival compared to Mock or FL-DCs pulsed with mock-infected N18 (p=0.005 and p=0.006, respectively; log rank test) (FIG. 3A). CTL activity was determined using a caspase 3 cleavage assay (He et al., J. Immunol. Methods, 304:43-59, 2005). Briefly, splenocytes of two mice vaccinated with G47Δ-infected N18 or RPMI were harvested 14 days after vaccination, restimulated with irradiated N18 (40 Gy) for 5 days, incubated for 3 hours with target N18 labeled with far red dye DDAO-SE (Molecular Probes) at different effector/target ratios, and activated caspase 3 positive target cells were determined by FACS. Mice vaccinated with FL-DCs pulsed with G47Δ-infected N18 cells rejected the tumors and induced CTL (FIG. 3B).

Example 3

Activation of DCs by Infected Tumor Cell Supernatants

Figure 4B:
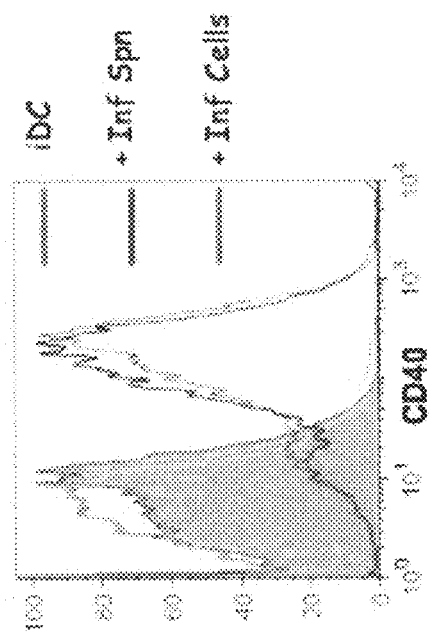

To determine what aspect of the infected cells is important to DC activation, we compared G47Δ-infected N18 cells with supernatant from the infected cells. FL-DCs pulsed with infected cell supernatant (1/10 dilution) matured as well as FL-DCs pulsed with infected cells. FL-DCs ($10^6$ cells/ml) were incubated overnight with either G47Δ-infected N18 supernatant diluted 10-fold (Inf Spn) or G47Δ-infected N18 cells (Inf Cells). Maturation of DCs was evaluated by analyzing expression of B7.1 (anti B7.1-PE; BD) (FIG. 4A) and CD40 (anti CD40-PE; BD) (FIG. 4B) on FL-DCs as determined by FACS (isotype controls: hamster IgG2 and rat IgF2 for B7.1 and CD40 respectively, filled pink). Pulsing FL-DCs with infected cell supernatant was just as effective at inducing DC maturation as pulsing with infected cells, including inducing IFN-alpha and IL-12 production.

IL-12 was predominantly synthesized in cDCs after pulsing FL-DCs. Immature FL-DCs were pulsed overnight with G47Δ- or mock-infected N18 supernatant (diluted 1/10), then Brefeldin A (3 μg/mL) was added for 5 hours and FL-DCs harvested, fixed and permeabilized (Fixation and Permeabilization kit, eBiosciences), and stained with anti-CD11b-FITC (BD), anti-B220-APC (BD) surface antibodies, and intra-cellular anti-IL12-PE (BD). As a control, FL-DCs were labeled with isotype antibodies to identify the positive and negative gates of matched antibodies. 52.7% of FL-DCs pulsed with G47Δ-infected N18 supernatant (FIG. 5B) synthesized IL-12 compared to 15.6% of mock-infected N18 supernatant pulsed FL-DCs (FIG. 5A). Among the IL12$^+$ FL-DCs, 71.8% are cDCs and only 3.9% pDCs (FIG. 5C). Among the IL-12$^-$ FL-DCs, approximately half were cDCs and half were pDCs (FIG. 5D).

Several secreted cytokines/chemokines were upregulated after FL-DC pulsing. Supernatants from FL-DCs pulsed overnight with G47Δ-(FIG. 6A) or mock-infected (FIG. 6B) N18 supernatant (diluted 1/10) were harvested and incubated overnight on membranes pre-coated with capture antibodies specific for 40 different cytokines and detection antibodies (Proteome Profiler™, R&D). Cytokine/detection antibody complexes were visualized using streptavidin-HRP substrate followed by chemiluminescent detection reagent (ECL Plus, GE Healthcare). Boxed duplicate spots were increased relative to mock. Many of the cytokines/chemokines increased relative to mock were inflammatory molecules produced by activated DCs (IP-10/CXCL10, MIP-1β/CCL4, MIP-1α/CCL3, CCL2, RANTES, MIG/CXCL9) (Lebre et al., Immunol. Cell Biol., 83:525-535, 2005; Decalf et al., J. Exp. Med., 204:2423-37, 2007).

Figure 7:
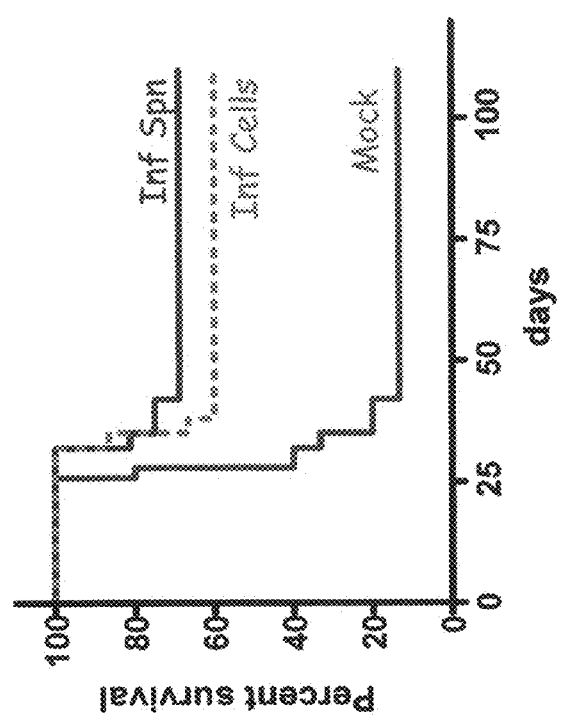
FIG. 7 is a line graph depicting percent survival of mice vaccinated subcutaneously with FL-DCs ($5 \times 10^5$/mouse) pulsed with G47Δ-infected N18 cells (n=15) (Inf Cells), FL-DCs pulsed with G47Δ-infected N18 supernatant (n=14) (Inf Spn), or RPMI (n=15) (Mock) 14 and 7 days before being challenged subcutaneously with N18 cells ($5 \times 10^5$/mouse).
Figure 8A:
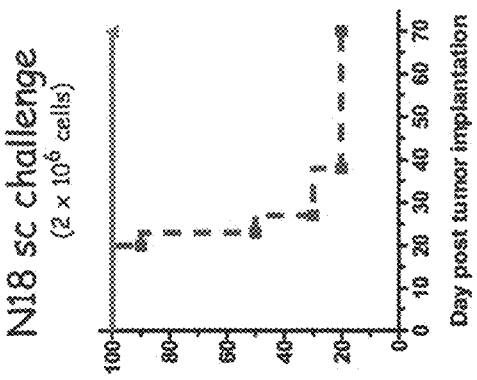
FIGS. 8A-8D are line graphs depicting percent survival of vaccinated and naïve mice challenged subcutaneously (8A-8C) or intracerebrally (8D) with tSCK mammary carcinoma cells (8A), N18 cells (8B), Neuro2a cells (8C), or N18 cells (8D).
Figure 8B:
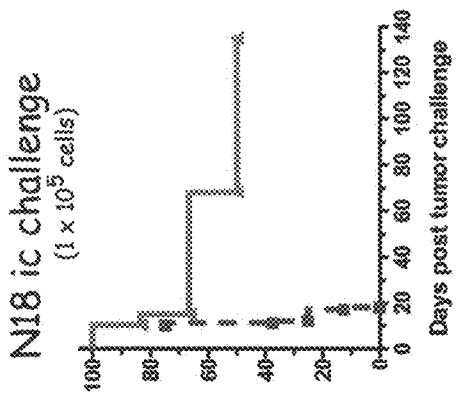
Figure 8C:
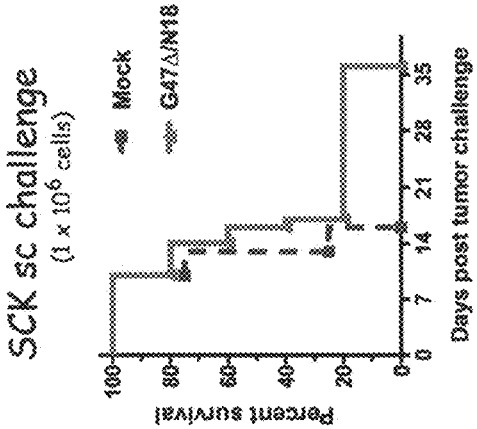
Figure 8D:
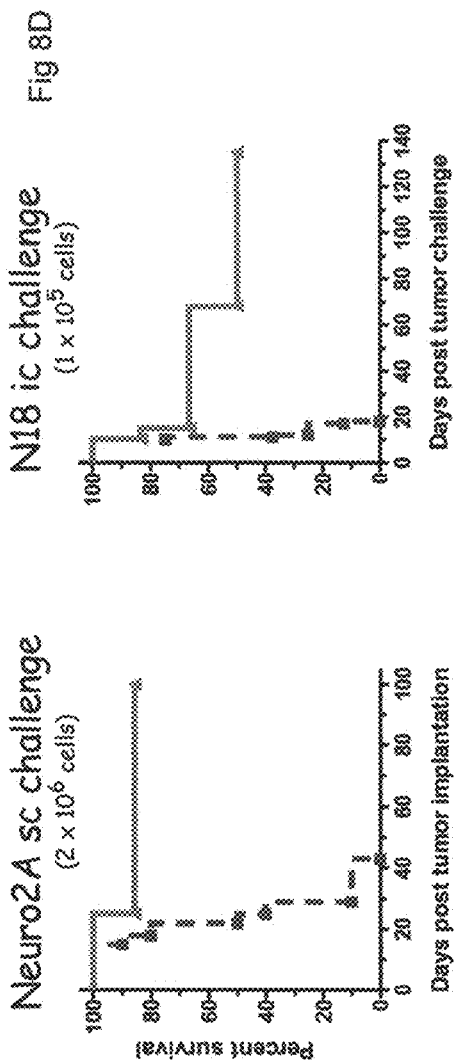

FL-DCs pulsed with infected cell supernatant were as effective as FL-DCs pulsed with infected cells in protecting against lethal tumor challenge, even long-term (memory). Mice were vaccinated subcutaneously with FL-DCs ($5 \times 10^5$/mouse) pulsed with G47Δ-infected N18 cells (n=15) (Inf Cells), FL-DCs pulsed with G47Δ-infected N18 supernatant (n=14) (Inf Spn) or RPMI (n=15) (Mock) 14 and 7 days before being challenged subcutaneously with N18 cells ($5 \times 10^5$/mouse). Survival was significantly improved in mice vaccinated with pulsed FL-DCs compared to mock, but not significantly different between pulsed FL-DCs groups. Vaccination with both infected cell and supernatant pulsed FL-DCs were similarly effective at inhibiting tumor growth, and prolonging survival (FIG. 7). Four months after the first tumor challenge, tumor-free mice, as well as naïve mice of the same age were rechallenged subcutaneously with an increased number of N18 cells ($2.5 \times 10^6$/mouse), and the number of tumor-free mice was determined (FIG. 8B). Tumor-free mice were also protected against intracerebral N18 challenge (p<0.02, Longrank test) (FIG. 8D). Tumor-free mice were also protected against a similar, but non-identical neuroblastoma tumor, Neuro2A (FIG. 8C), suggesting overlapping antigens. The immunity was tumor-specific, as rechallenge with a different syngeneic tumor, mammary carcinoma SCK, did not result in any protection (FIG. 8A). Therefore, vaccination provided long-term protection to lethal tumor rechallenge, including in the brain.

Example 4

G47Δ Acts as an Adjuvant to Activate FL-DCs

It was possible that residual G47Δ present in the supernatant could have provided a "danger" signal to induce DC activation. Therefore, we compared G47Δ-infected N18 supernatant with mock N18 supernatant plus low dose G47Δ (MOI=0.02). Immature FL-DCs were incubated with G47Δ-infected N18 supernatant (dil 1/10) or mock-infected N18 supernatant (dil 1/10) supplemented with G47Δ (same pfu as detected in supernatant of infected N18 ($10^4$ pfu/ml or 0.01 pfu/DCs)). The next day FL-DC maturation was assessed by flow cytometry with anti-MHC class I-PE (BD) (FIG. 9B) and anti-CD40-PE (BD) (FIG. 9C). Filled histograms represent isotype antibody controls (rat IgG2; BD). Addition of low dose G47Δ to mock supernatant was effective at inducing DC maturation. To determine whether DC induced to mature by G47Δ could provide protection in vivo, mice were vaccinated subcutaneously with FL-DCs ($5 \times 10^5$/mouse) pulsed with G47Δ-infected N18 supernatant (n=14), mock-infected N18 supernatant with G47Δ (n=12) or RPMI (n=14) 14 and 7 days before challenge subcutaneously with N18 cells ($5 \times 10^5$/mouse). Survival was significantly improved in mice vaccinated with FL-DCs pulsed with mock-infected N18 supernatant with G47Δ compared to mock-treated (p=0.002, Logrank test), but was significantly decreased compared to G47Δ-infected N18 supernatant (p=0.001, Logrank test) (FIG. 9A). Although addition of low dose G47Δ to mock supernatant could induce DC maturation, the mature DCs thus produced did not provide effective protection in vivo.

Rather than using tumor cell supernatants plus G47Δ to pulse FL-DCs, we tested cell lysates (for example freeze/thaw, sonication), which liberate most cell constituents, plus G47Δ. Cell lysate supernatants were obtained from irradiated (15 Gy) N18 cell ($1 \times 10^6$/ml) that underwent three freeze thaw cycles and then sonication for 1 minute, followed by low speed centrifugation. Pulsing FL-DCs with N18 cell lysates alone did not induce maturation, as indicated by the lack of IFN-alpha or IL-12 secretion (FIGS. 10A, B). However, addition of low-dose G47Δ (MOI<0.1) induced some maturation, although less than pulsing with G47Δ-infected N18 supernatant (FIGS. 10A, B). FL-DCs pulsed with infected cell supernatants or lysate supernatants plus low-dose G47Δ were able to protect mice from a lethal tumor challenge (FIG. 10C).

To determine the effect of different doses of HSV, immature FL-DCs were incubated with N18 antigen supplemented with G47—(MOI=0.01, 0.1, and 1.0). The next day, FL-DC maturation was assessed by flow cytometry with anti-MHC class I-PE, anti-MHC class II-PE, anti-B7.1-PE, anti-B7.2-

PE, and anti-CD40-PE. The three dosages of G47delta were all about equally effective at inducing DC maturation.

Example 5

Mouse Glioma Model

Figure 11C:
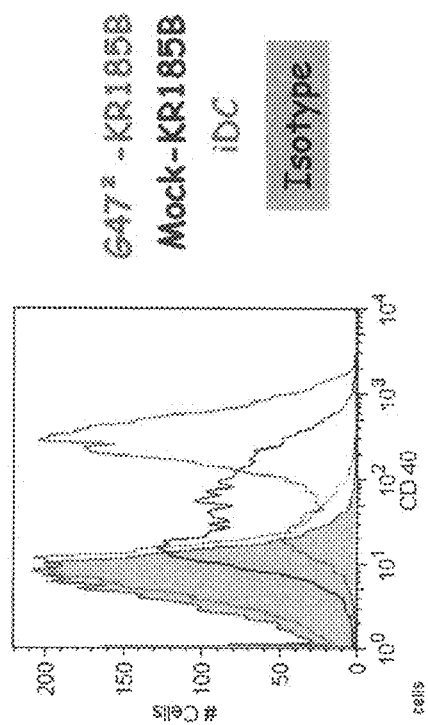
FIG. 11C is a histogram of CD40 expression of immature FL-DCs (iDC) or immature FL-DCs pulsed overnight with KR158B infected with G47Δ at a MOI=0.3 (G47Δ-KR158B), mock infected KR158B (Mock-KR158B). Isotype controls are indicated for reference.
Figure 11B:
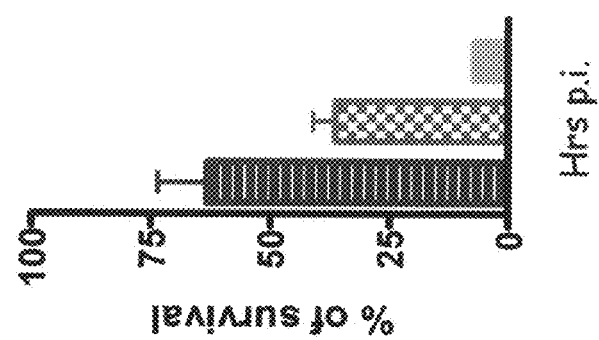
FIG. 11B is a bar graph depicting percent survival of KR158B infected with G47Δ at MOI=0.3 at 24, 48, and 72 hours post-infection.
Figure 11A:
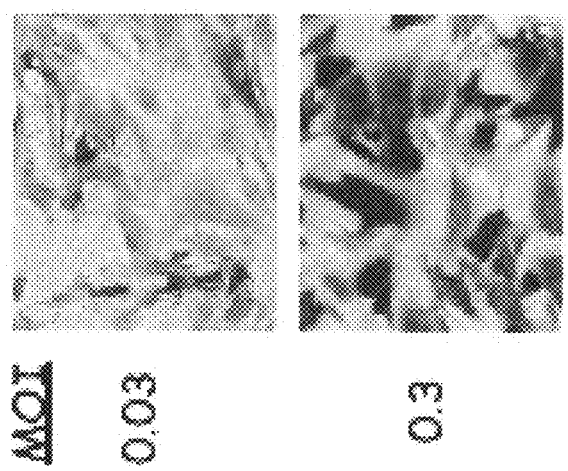
FIG. 11A is a pair of micrographs of KR158B cells infected with G47Δ at the indicated MOI for 90 minutes, incubated at 37° C., fixed 7 hours later and X-gal stained to detect virus infected cells.

A mouse glioma model was developed to examine immunotherapy in the brain. The KR158B cell line was derived from a glioma arising in NF1/p53 knock-out mice. To determine susceptibility to G47Δ infection, KR158B were infected at an MOI of 0.03 or 0.3 for 90 minutes, incubated at 37° C., fixed 7 hours later, and X-gal stained. Virus infected cells were detected (FIG. 11A). KR158B was also found to be susceptible to G47Δ infection and cytotoxicity. KR158B were infected at MOI=0.3, and cell viability determined was determined at 24, 48, and 72 hours as described in Example 1 (FIG. 11B). Fewer than 50% of the cells survived at 48 hours, and fewer than 25% survived at 72 hours.

G47Δ-infected mouse KR158B glioma cells were also able to stimulate immature FL-DCs to mature. KR158B infected at a MOI=0.3 were used to pulse immature FL-DCs overnight, which were then analyzed by flow cytometry for CD40 expression. G47Δ-infected glioma cells matured better than Mock infected tumor cells (FIG. 11C).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject for a brain tumor comprising:
   administering to the subject a composition comprising mature dendritic cells produced by incubating a population of immature dendritic cells generated from a sample obtained from the subject or a closely matched donor, with:
   (i) a brain tumor cell of the subject, infected with an effective amount of oncolytic herpes simplex virus (oHSV) G207 or G47Δ;
   (ii) a composition derived from a brain tumor cell of the subject infected with an effective amount of oHSV G207 or G47Δ, wherein the composition is selected from the group consisting of supernatant, conditioned medium, eluate, and lysate;
   (iii) A brain tumor cell of the subject and an effective amount of oHSV G207 or G47Δ; or
   (iv) a composition derived from a brain tumor cell of the subject and an effective amount of oHSV G207 or G47Δ, wherein the composition is selected from the group consisting of supernatant, conditioned medium, eluate, and lysate;
   to thereby produce mature dendritic cells;
   to thereby treat the subject for the brain tumor.

2. The method of claim 1, wherein the oHSV expresses an immunomodulatory transgene that encodes the immunomodulatory agent selected from the group consisting of Flt-3 ligand, CCL17, IL-18, HMGB1, and calreticulin.

3. The method of claim 1, where in the population of immature dendritic cells comprises plasmacytoid dendritic cells and conventional dendritic cells.

4. The method of claim 1, wherein the population of immature dendritic cells is generated from culturing bone marrow progenitor cells of the subject with Flt-3 ligand.

* * * * *